United States Patent [19]
Braatz et al.

[11] Patent Number: 5,381,836
[45] Date of Patent: Jan. 17, 1995

[54] FLUID DELIVERY SYSTEM

[75] Inventors: Robert E. Braatz, Sun Prairie, Wis.; Raymond S. Gregory, Bingley, Great Britain; Robert A. Heaton, Skipton, Great Britain; Keith Whitaker, Keighley, Great Britain; David C. Sampson, Cowling, Great Britain

[73] Assignee: The BOC Group plc, Windlesham, England

[21] Appl. No.: 90,216

[22] PCT Filed: Jan. 24, 1992

[86] PCT No.: PCT/GB92/00140
§ 371 Date: Jul. 23, 1993
§ 102(e) Date: Jul. 23, 1993

[87] PCT Pub. No.: WO92/12753
PCT Pub. Date: Aug. 6, 1992

[30] Foreign Application Priority Data
Jan. 24, 1991 [GB] United Kingdom ................. 9101560

[51] Int. Cl.6 ............................. B65B 1/04; B65B 3/04
[52] U.S. Cl. ........................................ 141/21; 141/286; 141/292; 141/352; 141/366; 128/200.21; 137/614.04; 137/588
[58] Field of Search ................. 141/21, 198, 285, 286, 141/290, 291, 292, 293, 351, 352, 363, 364, 365, 366, 346, 348, 349; 128/200.19, 200.16, 200.21; 137/614.04, 588

[56] References Cited
U.S. PATENT DOCUMENTS

| 1,802,523 | 4/1931 | Morangier | 141/352 |
| 3,540,402 | 11/1970 | Kocher | 141/292 |
| 3,797,262 | 3/1974 | Eigenbrod | 141/5 |
| 4,813,454 | 3/1989 | Smith, III | 137/614.04 |
| 4,867,212 | 10/1989 | Mohr et al. | 141/290 |

FOREIGN PATENT DOCUMENTS

| 0242979 | 10/1987 | European Pat. Off. . |
| 0295671 | 6/1988 | European Pat. Off. . |
| 0448954 | 2/1991 | European Pat. Off. . |
| 2028653 | 9/1970 | France . |
| 8429005 | 2/1985 | Germany . |
| 9015951 | 12/1990 | WIPO . |

Primary Examiner—Henry J. Recla
Assistant Examiner—Steven O. Douglas
Attorney, Agent, or Firm—Roger M. Rathbun; Larry R. Cassett

[57] ABSTRACT

A system for delivery of volatile liquid drugs as supplied to a patient by an anaesthetic vaporizer comprises a supply container (2) and a vaporizer (32) which includes a sump. Each of the supply container and the vaporizer is provided with a valve assembly (6, 34) which, when closed, prevent passage of fluid from the supply container into the sump. The supply container and the sump are connected to one another by means of a bayonet connection, which is made when indexing elements on the containers correspond. The valve assemblies in the containers are opened when the containers are connected to one another by means of an insert (40) located within an inlet conduit (10) linking the two containers.

The inlet conduit (10) is rotatable between lowered and raised positions, to open a valve (37) by which flow of fluid into and out of a reservoir for fluid in the sump can be controlled.

9 Claims, 9 Drawing Sheets

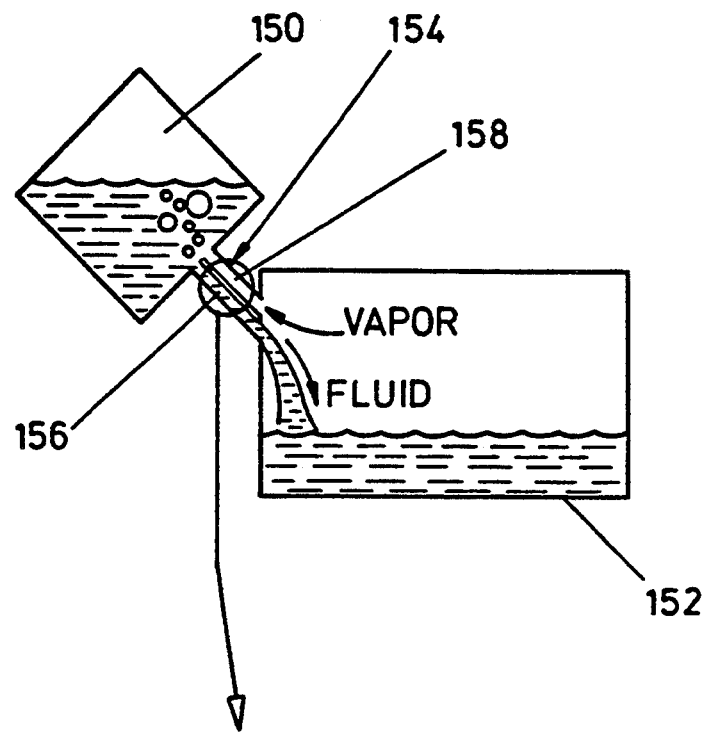
FIG. 8A
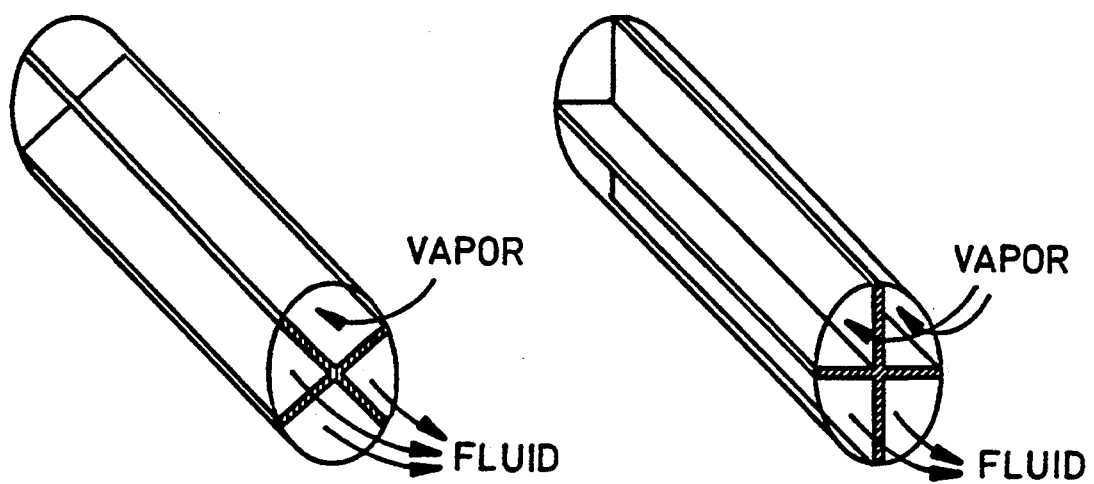
FIG. 8B
FIG. 8C

FLUID DELIVERY SYSTEM

This invention relates to a fluid delivery system for delivery of volatile liquid drugs such as might be used in anaesthesia.

A requirement of a fluid delivery system used in the delivery of drugs, especially of anaesthetic agents, is that the system should be sealed, both to minimise loss of drug, and to prevent ingress of contaminants. This concern is particularly applicable in the case of volatile drugs, which can be lost through evaporation on exposure to atmosphere.

GB-1193241 and GB-1394216 disclose filling systems for use with anaesthetic vaporising apparatus, in which anaesthetic drug is supplied to the apparatus from a bottle by means of a flexible conduit. A risk of losing drugs through evaporation exists when using the filling systems disclosed in GB-1193241 and GB-1394216 because of the nature of the connection between the bottle from which drug is supplied and the conduit: the connection is made between the end of the conduit and the bottle after the relevant closure cap has been removed from the bottle.

Another problem with the known system is that liquid can be freely dispensed from the supply container simply by pouring it into an appropriate receiving container.

The present invention seeks to provide a fluid delivery system having improvements over previously used systems, in which means are provided to prevent loss of agent from a container in which the agent is supplied to a vaporiser, and from the vaporiser whether at the inlet to the vaporiser or from ths sump or both.

In one aspect, the invention provides a delivery system for delivery of an anaesthetic agent to an anaesthetic vaporiser, comprising:

(a) a supply container which includes an outlet for the agent and a valve assembly which includes a valve member for closing the outlet to minimise loss of the agent from it, the outlet having a first sealing surface associated with it; and (b) an anaesthetic vaporiser having a sump for anaesthetic agent and an inlet through which the agent can be received into the vaporiser, and a second sealing surface associated with the inlet which cooperates with the first sealing surface on the outlet from the supply container;

the valve member being openable to allow flow of the anaesthetic agent from the supply container only when a seal is made between the first and second sealing surfaces, on the supply container and the vaporiser respectively.

This delivery system has significant advantages over prior systems. In particular, the system allows a volatile liquid drug to be supplied to dispensing equipment in such a way that drug is not lost from the container in which it is supplied to that equipment.

Preferably, the valve assembly has indexing elements associated with it, by which the supply container can be identified, and the inlet to the vaporiser has indexing elements associated with it by which the vaporiser can be identified. Means for connecting the supply container and the vaporiser can then be provided which allow the supply container and the vaporiser to be connected to one another only when the indexing elements correspond, opening of the valve member being possible only when the supply container and the vaporiser are so connected. The likelihood of an incorrect drug being supplied from the supply container to the vaporiser is minimised as a result of the functional connection between the valve (by which flow of fluid from the bottle is controlled) and indexing elements provided on the vaporiser: in contrast to prior filling systems in which an indexing element was provide solely for identification purposes, in the present system, the indexing elements are associated directly with the valve by which the supply container is closed. As a result, fluid cannot be supplied from the container through the valve unless the indexing elements of the valve have been mated with corresponding indexing elements. Furthermore, fluid cannot be dispensed from the supply container by pouring freely into a vaporiser. An indexed connection to the supply container must be made before fluid can be dispensed.

Preferably, the valve on the supply container is caused to open as a direct result of the seal between the sealing surfaces being made. For example, when the valve member comprises a plate which is forced against an aperture by pressure of fluid within the supply container or by a spring or both, it can be opened by forcing the plate away from the aperture against the force exerted by the fluid. Such force could be applied as a result of the supply container being urged towards the vaporiser on making the seal (and optionally a connection) between the two. Another type of valve which might be used comprises apertures in two surfaces which can be rotated relative to one another. The valve is open when the apertures in the plates are aligned. In this embodiment, the rotation required to open the valve might be part of forming the seal between the two containers.

Preferably, the supply container includes means for forming a connection between the container and a vaporiser to retain the container on the vaporiser. This can allow the seal between the container and the vaporiser to withstand pressure within either or both of them, to which the seal is exposed when fluid is able to pass between them. A connection between the supply container and the vaporisor might be made by means of, for example, a bayonet fitting, a screw threaded fitting, a push fit with appropriate latches, a push fit with a threaded ring collar, and so on.

Preferably, the means for connecting the supply container to the vaporiser comprises a formation which presents a surface facing in a direction substantially opposite to the direction in which fluid passes out of the reservoir through the outlet. The surface may be provided by, for example, a flange, or one or more recesses or even a screw thread. The surface may face directly opposite to the direction in which the fluid flows, or at an angle to that direction, provided that there is an edge which can be engaged by engaging means on the vaporiser. Preferably, the surface extends around the entire perimeter of the container, so that the connection means is able to function irrespective of the rotational orientation of the container.

A formation of this type can be engaged by a pair of elements mounted on the vaporiser spaced apart by a distance which is less than the transverse dimension of the formation, for example by the side edges of a slot defined by, for example an aperture formed in a plate, or by a pair of appropriately spaced rods or bars.

The indexing elements provided on the supply container and the vaporiser may be provided as elements of the connection means. For example, when the supply container and the vaporiser are connected by means of a bayonet-type fitting, indexing might be provided by appropriate design of the cooperating flanges on the two components of the bayonet fitting. When the connection means involves a push-fit connection between the supply container and the vaporiser, indexing elements can be provided in the form of formations on the mating parts of the container and vaporiser. For example, such formations might be in the form of corresponding flanges or pins and grooves, or by selection of appropriate cross-section shapes (for example, circular, triangular, square, hexagonal, etc.), or sizes or both.

The valve assembly will generally be attached to the supply container when the supply container is filled with the fluid. It will generally be attached in such a way that it will be apparent if the attachment between the assembly and the container has been tampered with. For example, it might be attached by means of an adhesive or by forming a weld, or by means of a crimped ferrule.

Preferably, the valve assembly includes means for directing flow of fluid supplied from the supply container. The flow direction means may be in the form of a conduit which can function as a nozzle extending from the valve member. The flow direction means will generally engage directly the inlet to the vaporiser on the anaesthetic vaporiser. For example, a nozzle may be received in an inlet having a wider bore than the nozzle, the seal between the nozzle and the inlet being formed, for example, by means of an O-ring on the outer surface of the nozzle and the internal circumferential surface of the inlet. The reverse arrangement could, of course, be used instead.

Flow direction means provided as part of the valve assembly may include an element by which the valve is opened, as a result of connection between the supply container and the vaporiser being made.

In another aspect, the invention provides a delivery system for delivery of an anaesthetic agent to an anaesthetic vaporiser, comprising:
(a) a supply container which includes an outlet for the agent and a valve assembly which includes a valve meter for closing the outlet to minimise loss of the agent from it; and
(b) an anaesthetic vaporiser having a sump for anaesthetic agent and an inlet through which the agent can be received into the vaporiser, and a valve assembly associated with an inlet by which flow of fluid into the vaporiser can be controlled; and
(c) means by which a seal can be made between the supply container and the vaporiser to allow fluid flow between them;
the valve assemblies in the supply container and the vaporiser being operable in a single step.

The provision of separate valves associated with supply container and the vaporiser has the advantage that loss of fluid both from within and from between the supply container and the vaporiser is minimised. This concern is particularly appropriate in the case of low boiling point liquids, and of gases. The desire to minimise loss of fluid is strong in the cases of expensive fluids, and of fluids which might have undesirable effects if they escape; for example, in the case of a fluid having anaesthetic properties, fluid which escapes might induce mild drowsiness in people exposed to the escaping fluid.

In the delivery system according to this aspect of the invention, the two valves, provided on the supply container and the vaporiser respectively, are arranged to be opened and closed by a single moving operation. This might involve, for example, pushing valve plates away from respective apertures, against which they are forced by fluid under pressure in the supply container and the vaporiser. This engagement has the advantage that the number of steps to be performed by an operator of the system is minimised, while also achieving the desired minimised loss of fluid.

Preferably, the valves in the supply container and the vaporiser open as a direct result of the seal between the containers being made. For example, when valve members are displaced from their respective apertures, this might be achieved by drawing the container and the vaporiser towards one another as they become connected, with an insert between the valve members. The insert may prevent the valve members moving towards one another as the apertures and other components of the valve assemblies so move. As a result, the valves will be opened when the supply container and the vaporiser are moved towards one another.

The delivery system of this aspect of the invention preferably includes the indexing elements on the supply container and the vaporiser for correct identification of the supply container and the vaporiser, which are discussed in detail above.

In a further aspect, the invention provides a delivery system for delivery of an anesthetic agent to an anaesthetic vaporiser, comprising an anaesthetic vaporiser which comprises:
(a) a sump which has a valve for controlling flow of fluid into and out of the sump; and
(b) an inlet conduit through which fluid supplied from a supply container can enter the sump;
the conduit being moveable to operate the valve between a first position in which the valve is closed, and a second position in which the sump and the valve is open.

According to this aspect of the invention, a valve is provided for controlling flow of liquid into and out of the sump, the valve being operable by movement of a conduit through which liquid flows into the sump. The conduit will generally be connected to a supply container, for example indirectly by means of a receptacle in which the outlet from the supply container is received or directly, so that the valve provided in the sump is opened by movement of the supply container, together with the conduit.

Preferably, the inlet to the conduit is directed downwardly from the vaporiser when the conduit is in its first position and the valve is closed; it is preferred also that the inlet is directed upwardly from the vaporiser when in its second position and the valve is open. This has the advantage that collection of debris in the inlet while the inlet is not connected to a supply container is reduced. Furthermore, with the supply container being offered upwardly, the likelihood of liquid leaking from it before and during making a seal between the container and the conduit is small.

Preferably, the vaporiser includes means for engaging a supply container, provided at or towards the end of the inlet conduit remote from the sump. The engaging means may include means by which the conduit can be sealed, and preferably also connected, to a supply container. The engaging means might include, for example, a collar in which a supply container can be received.

Preferably, the vaporiser includes means for guiding the supply container engaging means during the rotational movement of the inlet conduit. Preferably, the guide means includes a formation which is engaged by the supply container engaging means when the inlet conduit is in its first position to prevent movement of the inlet conduit towards its second position. The guide means may take the form of a pair of rails, as might be provided by for example an elongate slot, the supply container engaging means moving between the rails. The guide means may include a formation which is engaged by the supply container engaging means when the inlet conduit is in its first position to prevent movement of the inlet conduit towards its second position. For example, when the guide means is provided by a pair of rails, the formation may be provided by a widened portion of the gap between the rails in which the supply container engaging means is received when the inlet conduit is in its first position. For example, guide means can be provided which has the form of a key-hole shaped slot. It can be convenient for the engaging means to be biased into engagement with the supply container engaging means. The engaging means can also be used to prevent inadvertent detachment of the supply container from the inlet conduit, for example by arranging for the engaging means to engage formations such as a pair of lugs or a recess on the supply container as the inlet conduit is moved from its first position towards its second position.

Appropriate seal means provided as part of the engaging means might include, for example, a rubber O-ring on the internal surface of the inlet conduit, for example on the internal surface of a collar, which engages a sealing surface on the external surface of a nozzle connected at the outlet from a supply conduit. Connection means might be in the form of, for example, a bayonet-type fitting or a push-fit fitting and so on. Preferably, the sealing means is so arranged that the conduit can only be moved to its upward position (in which the valve is opened) once a seal has been made between the inlet conduit and a supply container. Use of the system would therefore involve making a seal between supply container and the inlet conduit while the conduit is in its first position and the valve is closed. This might involve, for example, offering the supply container upwardly to the conduit if the conduit faces downwardly in its first position. Once a seal has been made between the supply container and the conduit, or after the two have been connected to one another or both, the conduit is moved to its upward position, causing the valve to be opened. Fluid can then flow from the supply container to the sump. This arrangement has the advantages that the possibility of loss of fluid from the vaporiser through the valve and from supply container, and of contamination of fluid within the sump, due to opening the valve when not connected to an appropriate supply container, are minimised.

Preferably, the conduit is moved between its downward and upward positions by rotation.

The delivery system of this aspect of the invention has the advantage that, by appropriate design of the moveable conduit, the sump, and a supply container for use with them, the maximum level of fluid contained within the sump can be restricted to the level of fluid in the supply container when in the upwardly extending position. This can allow overfill of the sump to be avoided.

The fluid delivery system of this aspect of the invention preferably also includes the features of the delivery systems discussed above. Thus, it is preferred that the vaporiser has two valves for controlling flow of liquid into and out of the container. One of the valves is operated by movement of an inlet conduit between downward and upward positions. One, and preferably each, of the valves on the vaporiser is operable together with a valve on the supply container. One or each of the valves on the vaporiser is preferably operable as a direct result of making the connection between the vaporiser and a supply container. Thus, the connection between the vaporiser and the supply container may be made during and as a result of movement of the inlet conduit between the downward and upward positions.

In yet another aspect, the invention provides a delivery system for delivery of an anaesthetic agent to an anaesthetic vaporiser, comprising:
(a) an anaesthetic vaporiser which includes a sump for the anaesthetic agent;
(b) a conduit for connection to a supply container, and through which anaesthetic agent can be delivered to the vaporiser from the supply container, the conduit being divided at least at the end which communicates with vaporiser into at least two chambers extending towards the other end of the conduit, the conduit extending from the vaporiser at an angle of from about 0° to about 85° to the vertical, with a first one of the chambers for flow of anaesthetic agent vapour out of the vaporiser located above at least part of a second one of the chambers for flow of liquid anaesthetic agent into the vaporiser.

This aspect of the invention has the advantage that supply of a liquid, having a boiling point not much greater than ambient temperature, to the vaporiser in which that liquid is in equilibrium with vapour, the vapour having a significant vapour pressure, is facilitated. It is common for such vapour pressures to approach one bar at ambient temperature. It has been found that the use of a conduit for connecting the supply container to the vaporiser, which is divided into two or more chambers, provides a path for liquid to flow from the supply container to the vaporiser, and a path for vapour to pass from the vaporiser to the supply container.

The chambers may be provided by means of a partition within a conduit. The partition may extend across the conduit, in the manner of a wall. In another embodiment, the chambers may be coaxial, provided by means of a partition which defines a central chamber and an outer annular chamber around the central chamber.

Liquid flow takes place primarily through the lower chamber(s), while vapour flow takes place through the upper chamber(s), possibly accompanied by some flow in the opposite direction of liquid. This arrangement has the significant advantage that flow of liquid from the supply container to the vaporiser can take place without steps having to be taken to equalise vapour pressures between the sump and the supply container. Indeed, a higher vapour pressure in the sump than in the supply container can assist flow of liquid into the sump.

The conduit may include more than one upper chamber or more than one lower chamber or both. A preferred configuration of conduit has two coaxial chambers. Other configurations include one in which at least three chambers are provided, defined by partitions which extend from a common point. For example, when the conduit has a circular cross section, the conduit may be divided into three chambers, each subtending an angle of 120° at the centre of the conduit. In another embodiment, the conduit may be divided into four chambers by two partitions which are approximately perpendicular to one another. The use of a conduit which presents at least three chambers, or one in which two coaxial chambers are provided, has the advantage that at least one upper chamber, and at least one lower chamber, are always presented for fluid flow, irrespective of the orientation of the conduit.

Preferably, the conduit is divided into chambers throughout the whole of its length between the supply container and the sump. An insert comprising one or more partitions by which the conduit is divided into chambers may also serve to open the valves provided in the supply container or the vaporiser or both. For example, the valves may be opened as a result of the supply container and the vaporiser being moved towards one another, in the manner described above, the insert in the conduit acting against the or each valve member and causing the or each valve member to be displaced from its respective aperture as the supply container and the vaporiser are moved towards one another, thereby opening the or each valve. The insert may be able to move within the conduit. This can facilitate use of the insert to open valves. The insert may be provided in more than one axial section, the sections being located adjacent to one another axially within the conduit. This can be particularly useful in the event that the conduit itself is provided in two sections, for example one section as part of a valve assembly on a supply container, and another section on the vaporiser, that section functioning as a receptacle for the conduit section of the supply container.

Fluids which might be delivered by the system of the present invention will generally be liquids. The invention is concerned in particular with liquids having a boiling point only slightly above ambient temperature, which are therefore volatile and likely to be lost by evaporation on exposure to atmosphere. The provision of a valve on a container from which such a liquid is supplied can minimise such loss, in addition to providing other advantages.

Anaesthetic agents which can be supplied to an anaesthetic vaporiser using the technique of the present invention include 2-chloro-1,1,2-trifluoromethyl difluoromethyl ether (sold under the trade names Enflurane and Ethrane), 1-bromo-1-chloro-2,2,2-trifluoroethane (Halothane and Fluothane), 1-chloro-2,2,2-trifluoroethyl difluoromethyl ether (Isoflurane and Forane) and fluoromethyl 2,2,2-trifluoro-1-(trifluoromethyl)ethyl ether (Sevoflurane). The technique of the invention is particularly well suited to the supply of 2-(difluoromethoxy)-1,1,1,2-tetrafluoroethane (sold under the trade names Desflurane and Suprane). Volatile low boiling points liquids are generally those having a boiling point less than about 5° C. above ambient temperature.

Embodiments of the present invention will now be described by way of example with reference to the accompanying drawings, in which:

FIGS. 8A–8C is an isometric view of an embodiment of conduit through which liquid can be supplied to a vaporiser from a supply container.

Figure 1:
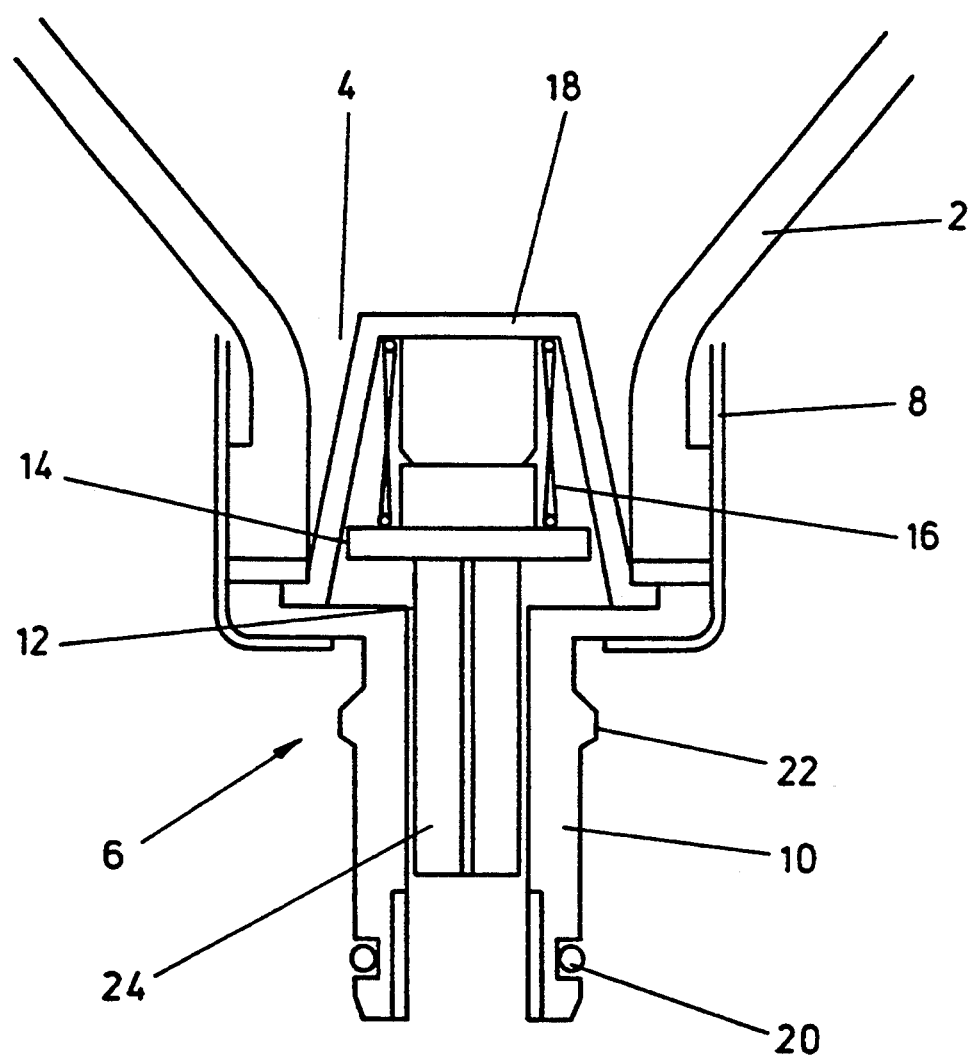
FIG. 1 is a schematic cross-section through an outlet from a supply container.

Referring to the drawings, FIG. 1 shows a supply container 2 for a liquid anaesthetic agent, the container being in the form of a bottle. The outlet 4 from the bottle is closed by means of a valve assembly 6. The valve assembly is attached to the bottle outlet by means of a crimped ferrule 8. The crimped ferrule makes it possible to detect any mistreatment of the seal between the valve assembly and the bottle.

The valve assembly comprises a conduit portion 10, through which fluid is supplied from the bottle 2. The opening 12 into the conduit 10 at the end proximal to the bottle 2 is closed by means of a moveable valve member 14. The valve member can move between a closed position in which it closes the aperture 12 and an open position as shown in FIG. 1. A spring 16 acts to force the valve member 14 towards the closed position. A cage 18 restricts movement of the valve member 14 in the open position.

At the end remote from the bottle 2, the conduit 10 has an 0 ring 20 provided in a groove.

On its external wall at a point between its two ends, the conduit 10 has an outwardly extending flange 22 around its perimeter.

Connected to the valve member 14 is an insert 24 which presents two partitions, dividing the conduit into four chambers. The two partitions extend across the conduit, the angle between them being about 90°. The application of force to the insert 24 in a direction towards the bottle 2 causes the valve to open, the force being applied against the force from pressurized fluid within the bottle 2, and against the force exerted by the spring 16.

Figure 2:
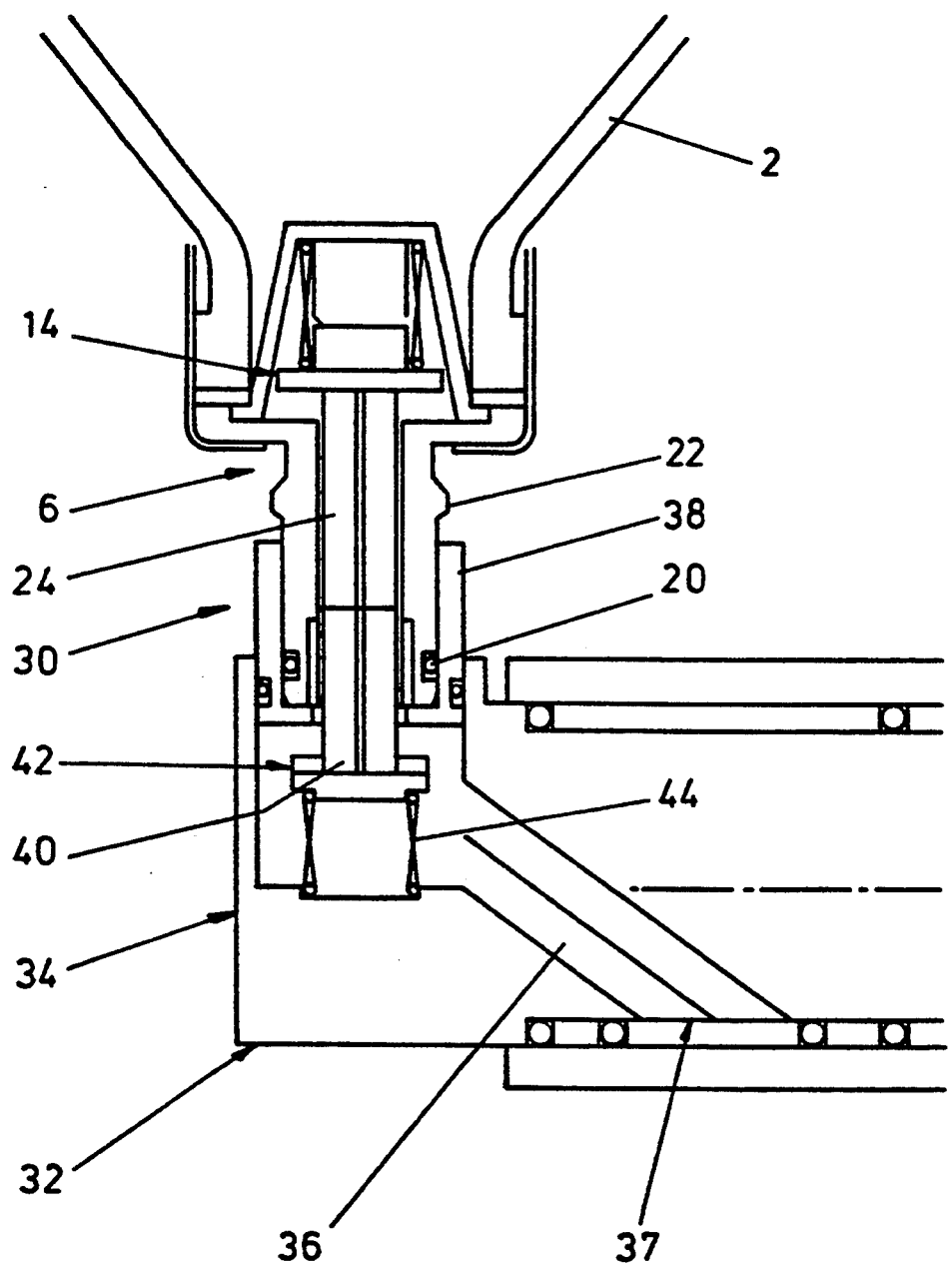
FIG. 2 is a schematic cross-section through the supply container shown in FIG. 1 connected to the inlet of a vaporiser.

FIG. 2 shows the bottle 2 and valve assembly 6 mounted on the inlet 30 of an anaesthetic vaporiser 32. The inlet 30 has a valve 34 provided within it which, when closed, prevents flow of fluid from the inlet into a conduit 36 which communicates via a valve 37 with the sump. In the open position (as shown), the valve 34 allows flow of fluid into the conduit 36.

The valve 34 includes a valve member 42 which, when the valve is closed, abuts the lower end (as shown) of the inlet conduit through which fluid enters the vaporizer. In this position, the valve is closed. As shown in FIG. 2, the valve member is displaced from the end of the inlet conduit, against the force exerted by the fluid within the vaporizer and force exerted by a spring 44.

The inlet 30 includes a receptacle 38 for the nozzle 10 on the bottle valve assembly 6. The O-ring 20 on the nozzle acts on a sealing surface on the internal surface of the receptacle to provide a seal between the nozzle and the receptacle 38.

An insert 40, which provides two substantially perpendicular partitions dividing the inlet conduit into four chambers, is slidable within the inlet conduit, together with the moveable valve member of the valve 34.

Means are provided for connecting the bottle 2 to the vaporizer 32, which act against the flange 22 on the conduit 10. An embodiment of the connection means is shown in FIG. 9 below. The connection means draw the bottle 2 towards the vaporizer 32 so that the inserts 24, 40 abut one another. Continued relative movement between the bottle and the receiving container causes the inserts to push the valve members of the valves 6, 34 to move away from their respective apertures, so that the valves open. Flow of fluid is then possible from the bottle 2 into the conduit 36, towards the vaporizer.

Figure 3:
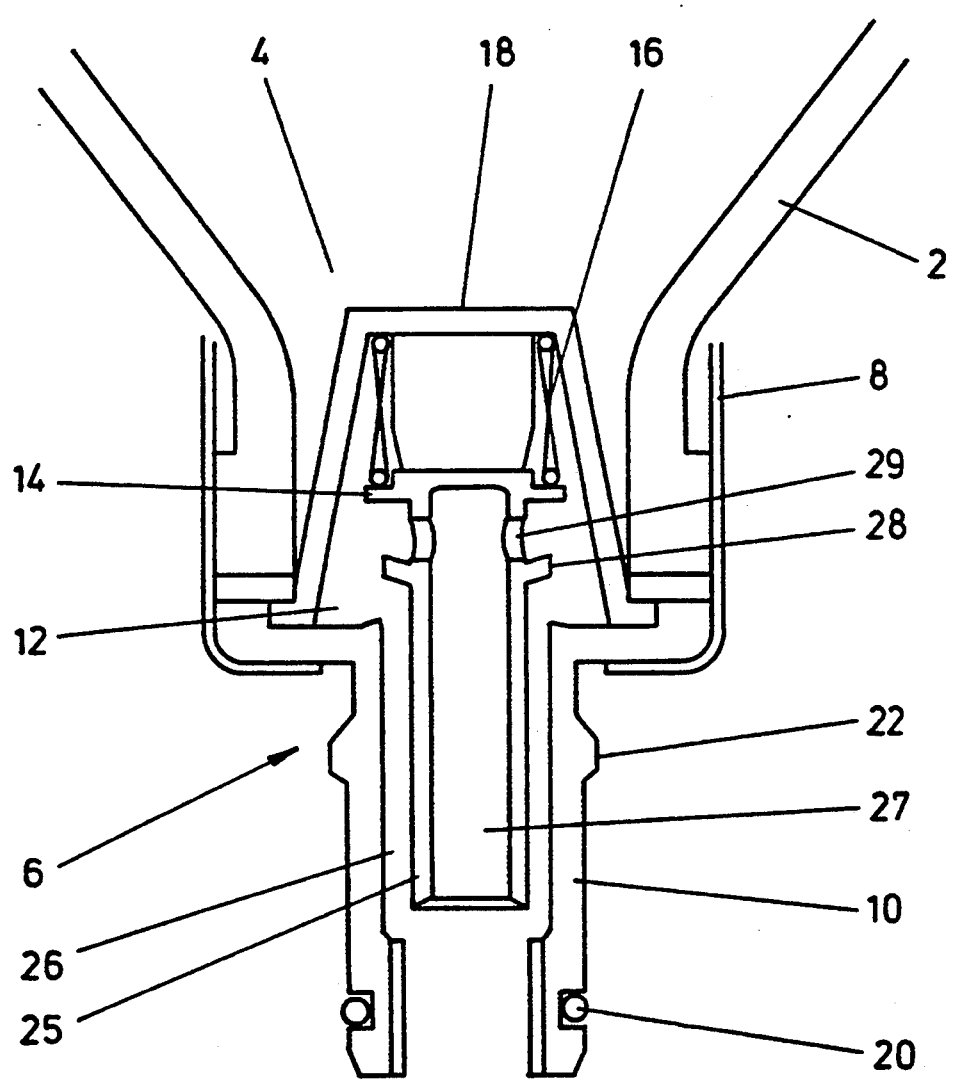
FIG. 3 is a schematic cross-section through another embodiment of outlet from a supply container.

FIG. 3 shows a supply container 2 in the form of a bottle. The outlet 4 from the bottle is closed by means of a valve assembly 6, which is attached to the bottle outlet by means of a crimped ferrule. The valve assembly comprises a conduit portion 10, through which fluid is supplied from the bottle 2. The opening 12 into the conduit 10 at the end proximal to the bottle is closed by means of a moveable valve member 14. The valve member can move between a closed position in which it closes the aperture 12 and an open position as shown in FIG. 3. A spring 16 acts to force the valve member 14 towards the closed position. A cage 18 restricts movement of the valve member 14 in the open position.

Attached to the valve member 14 is a cylindrical partition 25 which extends through the conduit 10, coaxially with it. The partition defines two coaxial chambers 26, 27 within the conduit. The outer chamber 26 is for flow of fluid, generally liquid, from the supply container 2 into the vaporizer, and the inner chamber 27 is for flow of fluid, which may be liquid or vapour, in the return direction. A deflector 28 can be provided towards the end of the partition adjacent to the valve member, to divide the flows of fluid in the two chambers, and ports 29 are provided through which fluid can pass out of the inner chamber 27.

Figure 4:
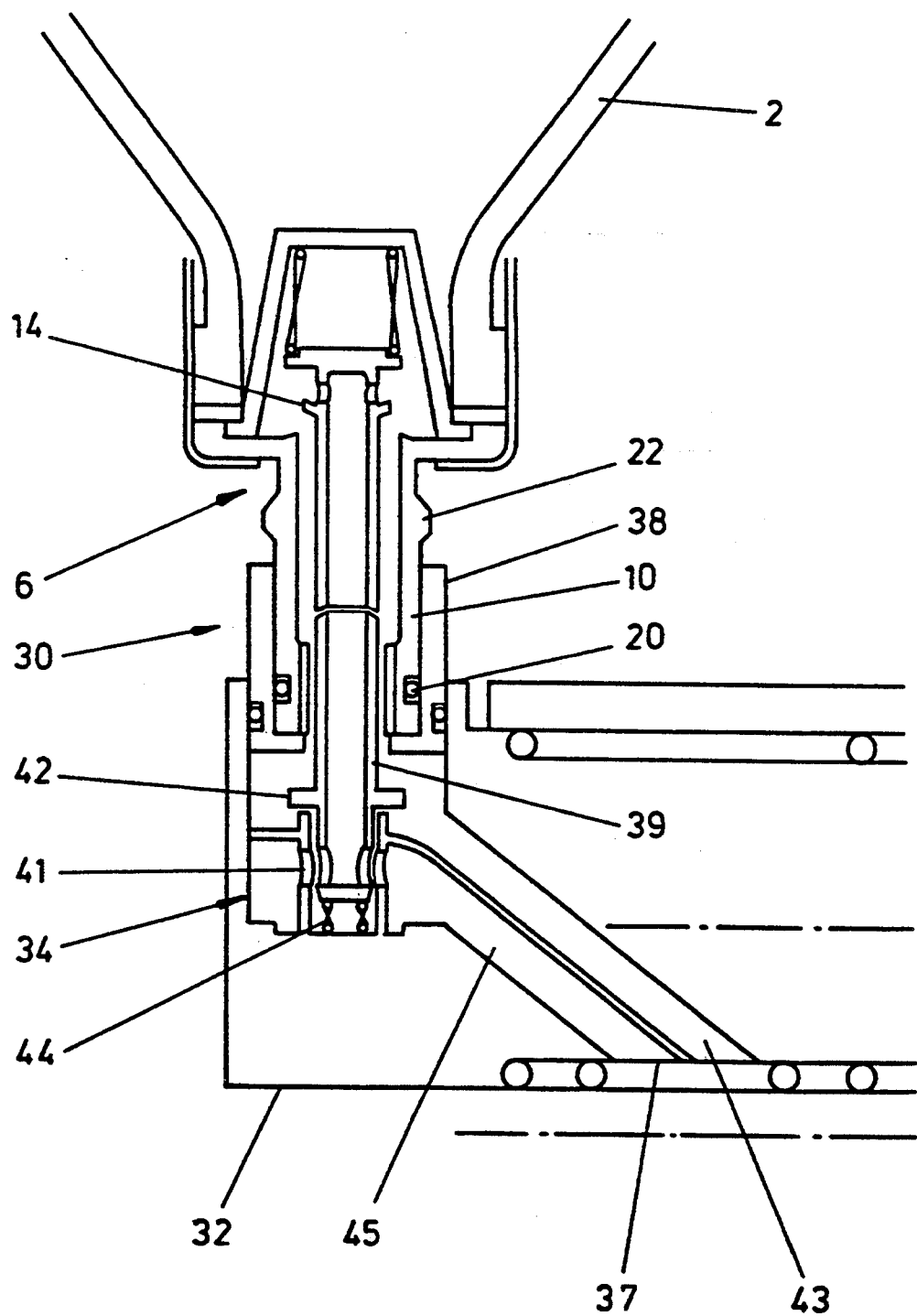
FIG. 4 is a schematic cross-section through the supply container shown in FIG. 3 connected to the inlet of a vaporiser.

FIG. 4 shows the bottle 2 and valve assembly 6 depicted in FIG. 3 mounted on the inlet 30 of an anaesthetic-vaporiser 32. The inlet 30 has a valve 34 provided within it, which includes a valve member 42 which, when closed, abuts the lower end (as shown) of the inlet conduit 10. In this position, the valve is closed and prevents flow of fluid between the inlet conduit and the sump. As shown in FIG. 4, the valve member is displaced from the end of the conduit 10, against the force exerted by the fluid within the vaporiser and force exerted by a spring 44. The inlet 30 also includes a cylindrical receptacle 38 for the nozzle 10 on the bottle valve assembly, and a cylindrical partition 39 which extends through the receptacle, coaxially with it. The partition defines two coaxial chambers within the receptacle, which communicate with the chambers 26, 27 defined by the partition 25 within the nozzle 10. The inner chamber terminates at ports 41 through which fluid can enter and leave that chamber.

Two passageways 43, 45 communicating with respective ones of the ports 41 from the coaxial chambers within the receptacle, allow flow of fluid between the vaporiser. The first passageway 43 provides for flow of fluid, generally liquid, from the supply container into the vaporiser, and the second passageway 45 provides for flow of fluid in the return direction.

Figure 5:
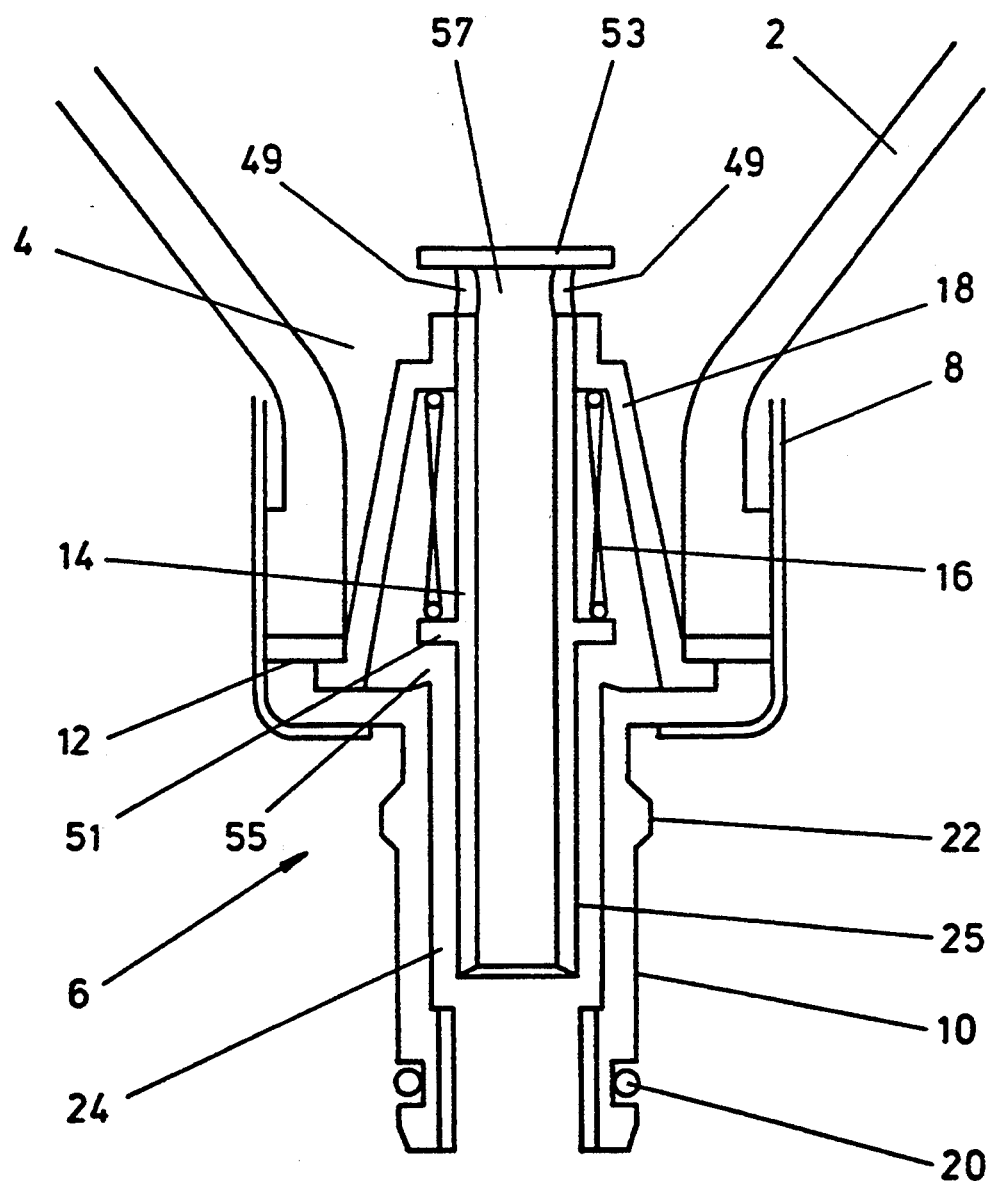
FIG. 5 is a schematic cross-section through a further embodiment of outlet from a supply container.

FIG. 5 shows a supply container 2 with an outlet 4 which is closed by means of a valve assembly 6. The valve assembly includes a conduit 10 which is closed by means of a moveable valve member 14. The conduit contains a cylindrical partition 25 which divides the conduit into two coaxial passageways. Access of fluid to the inner passageway is gained via ports 49. The valve member 14 can move between a closed position in which flanges 51, 53 closes openings 55, 57 into the passageways in the conduit 10, and an open position as shown in FIG. 5. A spring 16 acts to force the valve member 14 towards the closed position, and a cage 18 restricts movement of the valve member 14 in the open position.

Figure 6:
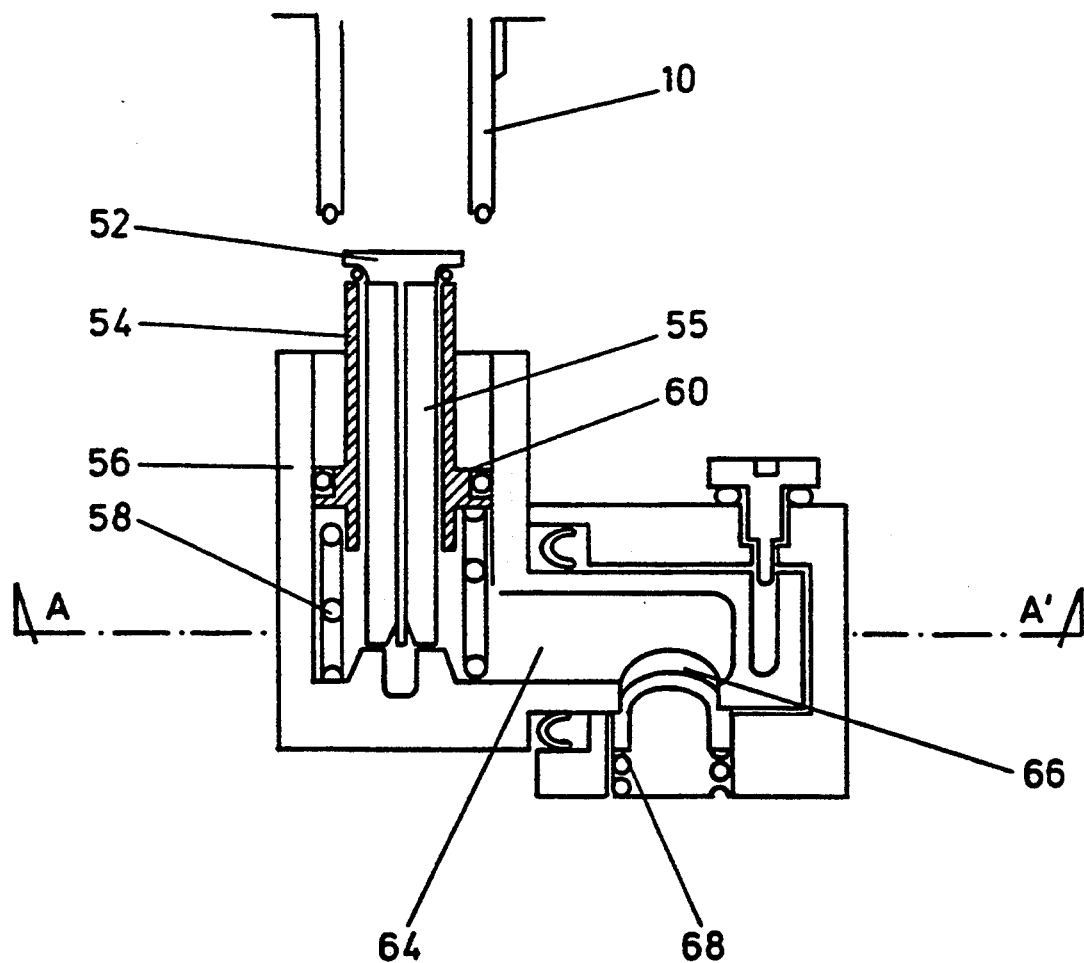
FIG. 6 is a cross-section through an alternative embodiment of inlet for a vaporiser.

FIG. 6 shows an alternative embodiment of an anaesthetic vaporiser. A valve member 52 is provided at an exposed end of an inlet conduit 54. An outlet conduit 10 on a bottle can receive the inlet conduit 54 and valve member 52 within it, the valve member then acting against an insert 24 within the outlet conduit 10 or directly against a valve member associated with the bottle valve assembly 6.

An insert 55 is provided within the inlet conduit 54 by which the conduit is divided into four chambers.

The inlet conduit 54 is slidable within a housing 56 on the receiving container against force exerted by a helical spacing 58. As the outlet conduit 10 on the bottle valve assembly 6 is positioned over the inlet conduit 54, it abuts an end wall 60, and forces the inlet conduit downwardly relative to the housing 56, the valve member 52, and the insert 55 within the insert conduit. As a result, an aperture between the insert conduit 54 and the valve member 52 is opened. Simultaneously, the valve member 40 in the bottle valve assembly 6 is moved relative to the opening 32, thereby allowing flow of fluid out of the bottle 2. The valve member 52 on the receiving container inlet may act directly against the valve member 14, or through an insert 24.

Fluid flowing from the bottle 2 through the inlet conduit 54 into the vaporiser, passes through a conduit 64 towards the vaporiser. The conduit 64 is mounted for rotation about the axis A–A' within a housing together with the inlet conduit 54. The conduit 64 within the vaporiser has an opening 66 formed in its side-wall through which fluid can pass out of the conduit into the sump, provided that the opening is aligned with a corresponding opening into the sump. In this way, rotation of the inlet conduit 52 and of a bottle mounted thereon can open a valve (provided by the openings from the conduit 64 and into the sump) makes it possible for liquid supplied from the supply container to enter the vaporiser. A spring loaded catch 68 can be used to locate the opening 66 relative to the opening into the sump.

Figure 7:
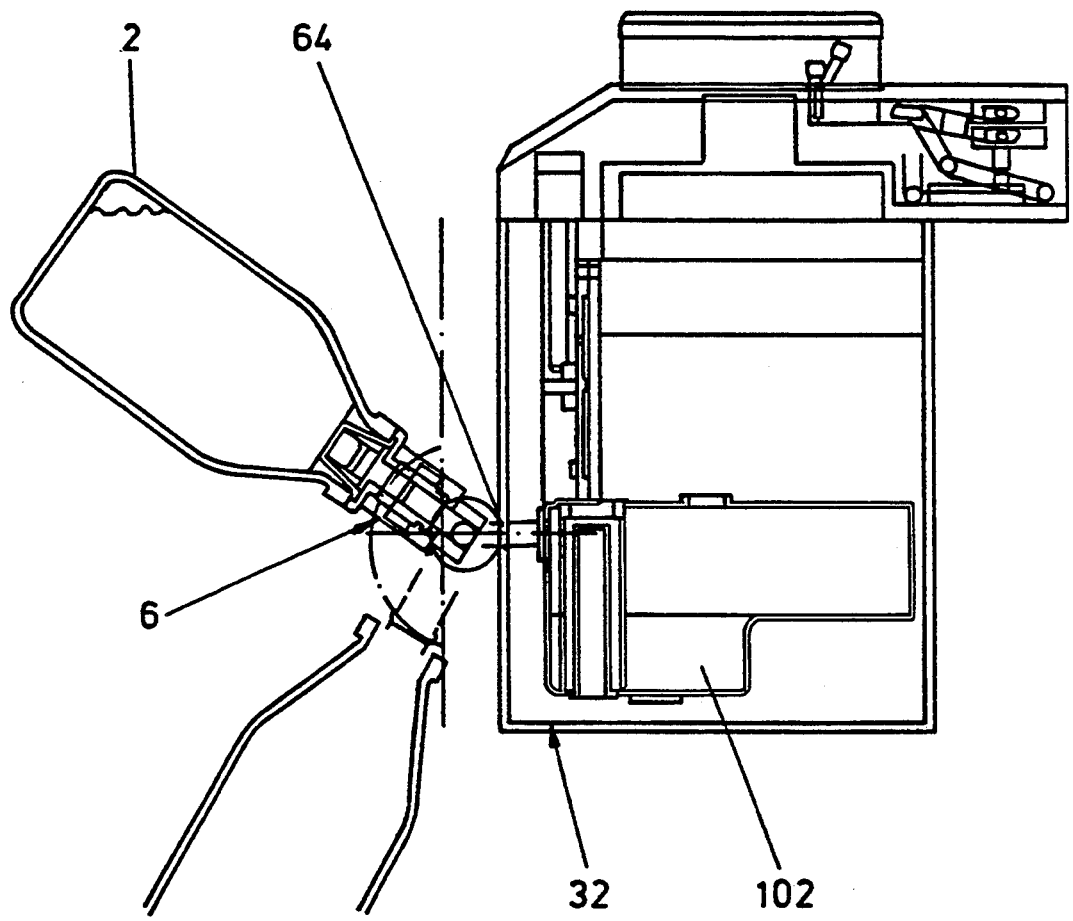
FIG. 7 is a schematic cross-section through a fluid delivery system which includes an inlet conduit which can be moved between two positions to open a valve, the inlet conduit being shown in each of its two positions.

FIG. 7 shows the bottle 2 connected to an anaesthetic vaporiser 32, which includes a sump 102. The bottle is shown in two positions, connected to an inlet conduit on the vaporiser. In a first position, the inlet conduit is directed downwardly from the vaporiser and sump. In this position, the bottle 2 can be connected to the vaporiser. Also in this position, the valve between the conduit 64 in the vaporiser and the sump 102, provided by the openings from the conduit and into the sump, is closed.

Movement of the bottle and inlet conduit from the lower position to the upper position causes:

the bottle to be moved towards the vaporiser and the sump so that the valves within the inlet and the bottle open, and the valve between the conduit within the vaporiser and the sump to open.

Flow of fluid from the bottle 2 into the sump 102 is possible once the bottle and the inlet conduit have been moved to the upper positions. The maximum level of fluid within the sump is restricted to the maximum level of fluid within the bottle. This minimises the possibility of overfilling the sump.

The invention makes it possible to prevent the supply of a wrong fluid from a supply container to an anaesthetic vaporiser. Indexing elements on the valve assembly 6 on the bottle 2, and on the inlet to the vaporiser and sump, ensure that the supply container and the vaporiser can only be connected to one another when the respective indexing elements correspond. Only when the supply container and the sump have been connected can the valves be opened to allow flow of fluid. The provision of valves ensures that fluid cannot be dispensed from the supply container other than through the indexed inlet conduit for the sump.

FIG. 8a shows schematically a supply container 150 and an anaesthetic vaporiser 152, with a conduit 154 connecting them. The conduit is divided into two or more chambers, at least one of the chambers being located above at least one other of the chambers. The conduit extends from the vaporiser towards the supply container at an angle of about 45° to the vertical. The lower chamber 156 of the conduit contains liquid passing from the supply container 150 to the vaporiser 152. The upper conduit 158 provides a path for flow of vapour from the sump to the supply container. This makes it possible for vapour pressure between the two containers 150, 152 to be equalised, and facilitates flow of liquid from the supply container to the sump.

FIGS. 8b and 8c show a preferred conduit in different orientations. Each conduit has a circular cross section, and contains an insert made up of two partitions arranged substantially perpendicularly to one another. The two partitions divide the container into four chambers. Whatever the orientation of the conduit, at least one of the chambers will be located above at least one of the other chambers within the conduit, thus providing respective pathways for flow of liquid and flow of vaporer.

Figure 9A:
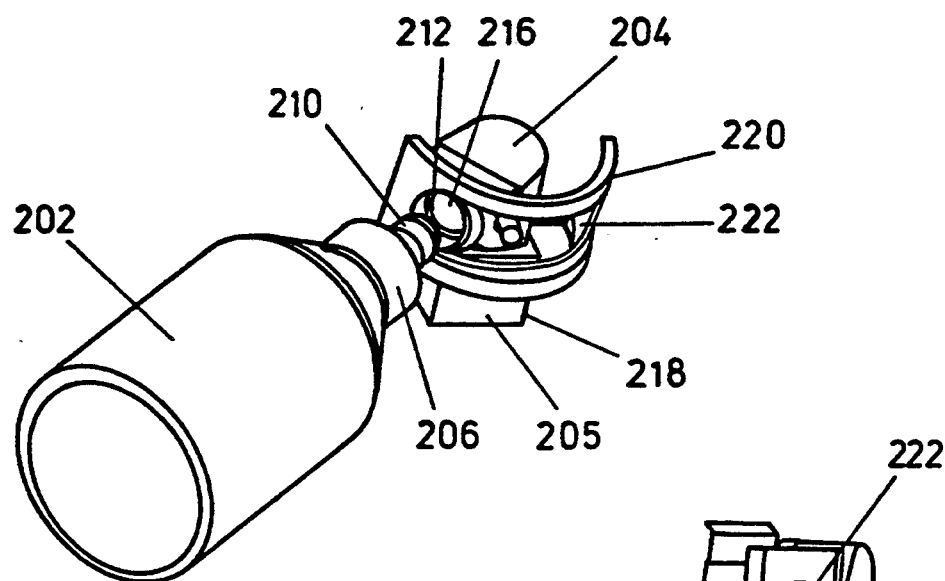
FIGS. 9A–9C shows views of a bottle for an anaesthetic agent, and an anaesthetic vaporiser to which the bottle can be connected.
Figure 9B:
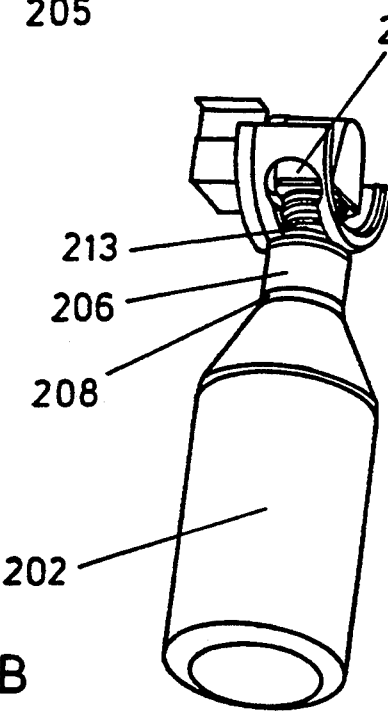
Figure 9C:
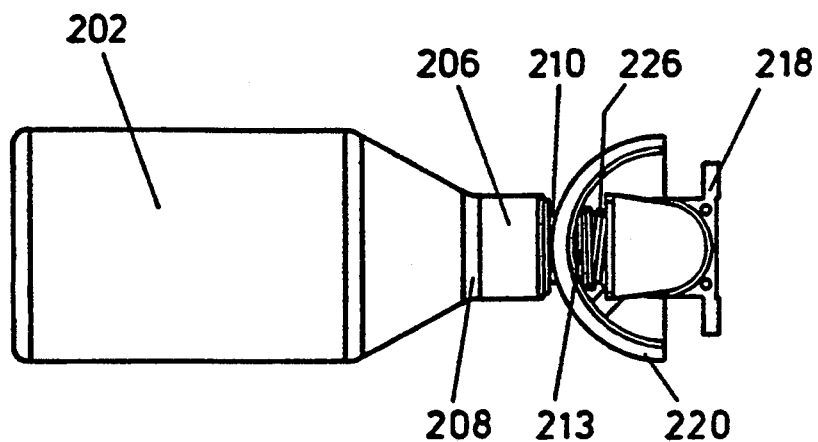

FIGS. 9a to 9c show views of a bottle 202 containing an anaesthetic agent under pressure, which is mounted on an inlet 204 to a sump in an anaesthetic vaporiser 205, for supply of the agent from the bottle into the sump.

The bottle 202 includes a valve assembly 206 which is clamped onto the mouth of the bottle by means of a ferrule 208, generally as described in FIG. 1 or FIG. 3 above. The valve assembly includes a valve member which, when the bottle is not connected to the sump, prevents escape of the agent from the bottle. It also includes a nozzle 210 by which flow of the agent from the bottle is directed. An O-ring 212 and an outwardly extending flange 213 are provided on the outer surface of the nozzle towards its free end.

The vaporiser 205 includes a inlet 214 for the free end of the nozzle 210 on the bottle. A valve, with an insert for opening that valve and the valve on the bottle, may be provided for example similar to those components of the vaporiser described with reference to FIG. 2. The inlet includes a receptacle 216 which contains a sealing surface on its internal surface against which the O-ring 212 acts to form a seal between the bottle and the vaporiser. The inlet is mounted for rotation about an axis B-B' on the housing 218 of the vaporiser (in which the pump is located), and contains a conduit through which anaesthetic agent entering the vaporiser from a bottle through the inlet passes into the sump. The conduit has at the end proximal to the housing an opening in its side wall, in the manner described with reference to FIG. 6. As a result, rotation of the inlet about the axis B-B' will cause the valve provided by the openings in the conduit and the sump to open.

The housing 218 has a guide 220 mounted on it for the rotation of the inlet 204. The guide has a key-hole shaped slot 222 provided in it, including a widened portion 224 at one end. The widened portion is able to receive the receptacle 216 in it, the receptacle being urged outwardly from the body of the inlet into the widened portion of the slot by means of a spring 226. The inlet is prevented from rotating relative to the housing of the vaporiser while the receptacle is so engaged in the widened portion of the slot as a result of the side walls of the slot engaging the sides of the receptacle.

The receptacle 216 can be caused to move against the force exerted by the spring 226 by insertion of the free end of the nozzle 210, so as to free the receptacle for movement along the slot 222 as the inlet is rotated relative to the vaporiser housing. As the inlet 204 and the bottle 202, whose nozzle has been inserted into the inlet, are rotated relative to the slot, the side walls of the slot 222 engage the flange provided on the free end of the nozzle, and retain the bottle engaged with the receptacle. This prevents the bottle from being forced away from the receptacle when connection between them is exposed to elevated pressure within the bottle and the sump.

The axis B-B' about which the inlet rotates relative to the housing is preferably horizontal. It is particularly preferred that the axis is arranged so that the inlet is moved upwardly to open the valve into the sump. Preferably, a bottle engaging the inlet requires to be held in the raised (valve open) position for the valve to, remain open, so that the valve is only open while an operator is present. If necessary, the receptacle may be biassed towards the downward facing position, for example by means of a spring which acts between the inlet and the housing.

We claim:

1. A delivery system for delivery of an anaesthetic agent to an anaesthetic vaporiser, comprising an anaesthetic vaporiser which comprises a sump which has a sump valve for controlling the flow of fluid into and out of said sump, an inlet conduit through which fluid supplied from a supply container can enter said sump, means for engaging the supply container, provided at or towards the end of the inlet conduit remote from said sump, said conduit being rotatably moveable to operate said sump valve between a first position in which said sump valve is closed, and a second position in which said sump valve is open, and means for guiding the supply container engaging means during the rotational movement of said inlet conduit.

2. A delivery system as claimed in claim 1, in which the guide means comprises an elongate slot.

3. A delivery system as claimed in claim 1, in which the guide means includes a formation which is engaged by the supply container engaging means when the inlet conduit is in its first position to prevent movement of the inlet conduit towards its second position.

4. A delivery system as claimed in claim 3, which includes a supply container for anaesthetic agent to be supplied to the sump, having an outlet through which the agent can leave the container.

5. A delivery system as claimed in claim 4, in which the supply container includes means for forming a connection between the container and the vaporiser to retain the container on the vaporiser.

6. A delivery system as claimed in claim 5, in which the connecting means comprises a formation which presents a surface facing in a direction substantially opposite to the direction in which fluid passes out of the supply container through the outlet.

7. A delivery system as claimed in claim 6, in which the vaporiser provides an elongate slot which can engage the formation.

8. A delivery system as claimed in claim 7, in which the slot is so configured as to draw the container towards the vaporiser as the container is moved along the slot.

9. A delivery system as claimed in claim 4, in which the supply container includes indexing elements by which it can be identified, and the vaporiser includes indexing elements by which it can be identified, the indexing elements on the supply container and the vaporiser corresponding to allow a seal to be made between the supply container and the vaporiser.

* * * * *